United States Patent [19]

Holtkamp

[11] Plant 5,023

[45] Apr. 5, 1983

[54] AFRICAN VIOLET PLANT

[76] Inventor: Reinhold Holtkamp, Werther Strasse 112, 4294 Isselburg, Fed. Rep. of Germany

[21] Appl. No.: 300,628

[22] Filed: Sep. 9, 1981

[51] Int. Cl.[3] ..... A01H 5/00
[52] U.S. Cl. ..... Plt./69
[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new cultivar of African violet known by the cultivar name Chicago, a sport of Nashville, disclosed in U.S. Plant Pat. No. 4,533. Chicago is characterized by its very compact growth habit, its girl-type leaves which are medium green with bright centers, with serrated edges, and by its basically white flowers which have purple centers and frequent purple stripes, with wavy or frilled edges, with the blossoms being single to semi-double and occasionally double in form.

1 Drawing Figure

The present invention comprises a new and distinct cultivar of African violet plant, botanically known as *Saintpaulia ionantha,* and hereinafter referred to by the culivar name Chicago.

The new cultivar which was referred to during the selection process by the designation d 150/4 M, and is a sport of the cultivar Nashville, disclosed in my U.S. Plant Pat. No. 4,533.

The new cultivar Chicago was discovered and selected by me as a flowering plant within a crop of the parent cultivar Chicago in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Chicago has not been observed under all possible environmental conditions. The phenotype may vary significantly with variations in environment such as temperature, light intensity and day length. The following observations, measurements and values describe the new cultivar as grown in Isselburg, West Germany, under greenhouse conditions which closely approximate those generally used in commercial practice.

The following traits have been repeatedly observed and are determined to be basic characteristics of Chicago, which in combination distinguish this African violet as a new and distinct cultivar:

1. Very compact leaves and corolla.
2. Petioles do not stretch if grown in tight space.
3. Girl-type leaves, medium green with bright center; serrated.
4. Seven or more upright flower stems, each carrying 7–11 or more flowers per stem.
5. Bicolor blossoms, basically white with purple center and frequent purple stripes, with wavy or frilled edges.
6. Single to semi-double and occasionally double blossom form.
7. Uniform growth habit.
8. Attractive saleable plant within 10 weeks after potting.

When compared with the parent cultivar Nashville, Chicago is also characterized by its compact growth habit, although Chicago is even more compact. The girl-type leaves are also similar to Nashville, as are the wavy or frilled petal edges. However, Chicago is distinguished from Nashville by the other characteristics noted above, principally by its varying blossom form and flower color.

The accompanying photographic drawing shows a typical specimen plant of the new cultivar. The colors appearing in the photograph are as true as possible with color illustrations of this type.

In the following description, color references are made to the Horticultural Colour Chart (HCC) issued by Wilson Colour Ltd., except where general colors of ordinary significance are referred to. Color values were taken under natural light conditions approximately midday in Isselburg, West Germany.

Botanical classification: *Saintpaulia ionantha,* Ramat. cv. Chicago.

Parentage: Sport of Nashville, disclosed in U.S. Plant Pat. No. 4,533.

Propagation: The new cultivar holds its distinguishing characteristics through successive propagations by leaf cuttings and by division of shoots.

Plant: From 5 cm. to 7 cm. tall when grown in pots, and approximately 15 cm. in diameter when fully grown.

Leaves:

- *General form.*—Girl-type, rounded, serrated, wavy.
- *Diameter.*—50–55 mm.
- *Texture.*—Tough and slightly shiny.
- *Aspect.*—Shiny.
- *Veins.*—Upperside well-visible; underside pronounced, velvety and hairy.
- *Color (upperside).*—HCC ivy green 0001060/3.
- *Color (underside).*—HCC willow green between 000862/2-1.
- *Petiole.*—HCC pod green 061/1, hairy.

Flowers:

- *Buds.*—Bell-shaped; 6 mm. just before opening; 7–11 or more per stem.
- *Sepals.*—Color: Bright green. Calyx: Flat, funneled. Aspect: Spear-shaped, slightly hairy. Peduncle: Short and strong.

Individual flowers:

- *Size.*—35–40 mm.

*Color.*—Upperside: Young flower right after opening sap green 62/3; changing to bright white with purple shades of doge purple 732/3 to 732. Underside: White with faint green tinge and shades of purple. Borne: Flower stem carries 7–11 or more flowers on short strong peduncles; flowers frequently display an additional small petal in center of bloom, and frequently appear semi-double to double.

*Shape.*—Conventional (2 small and 3 larger petals), slightly wavy with tiny frills.

*Flowering time.*—First flowers appear 8–9 weeks after potting; after 9–10 weeks full flowering saleable plant.

Reproductive organs:

*Stamens.*—2 (occasionally 3) anthers, composed of 2 cells, with seed capsule pushed slightly through.

*Anthers.*—HCC mimosa yellow 602.

*Filaments.*—3 mm. long; purple-green.

*Styles.*—6 mm. purplish; base of ovary medium green, hairy.

*Pollen color.*—HCC mimosa yellow 602/3.

Roots: White when young and active; greenish brown when older; normally developed.

Disease resistance: Good as experienced to date.

General observations: Chicago is a compact plant having distinctive girl-type leaves. Even in very tight growing space, the leaves do not stretch. The flowers of Chicago are a clear white with purple centers and frequent additional purple marking. Most blossoms are single, yet they also appear semi-double to double. They are non-dropping and long-lasting.

I claim:

1. A new and distinct cultivar of African violet known by the cultivar name of Chicago and distinguished by combined characteristics of very compact growth habit for both leaves and corolla; girl-type leaves, medium green in color with bright center and serrated on edges; 7 or more upright flower stems each of which carries 7–11 or more flowers per stem, with the flowers being basically white with purple centers and frequent purple stripes, and having wavy or frilled edges; single to semi-double and occasional double blossom form; uniform growth habit, and by its ability to provide an attractive saleable plant within 10 weeks after potting.

* * * * *

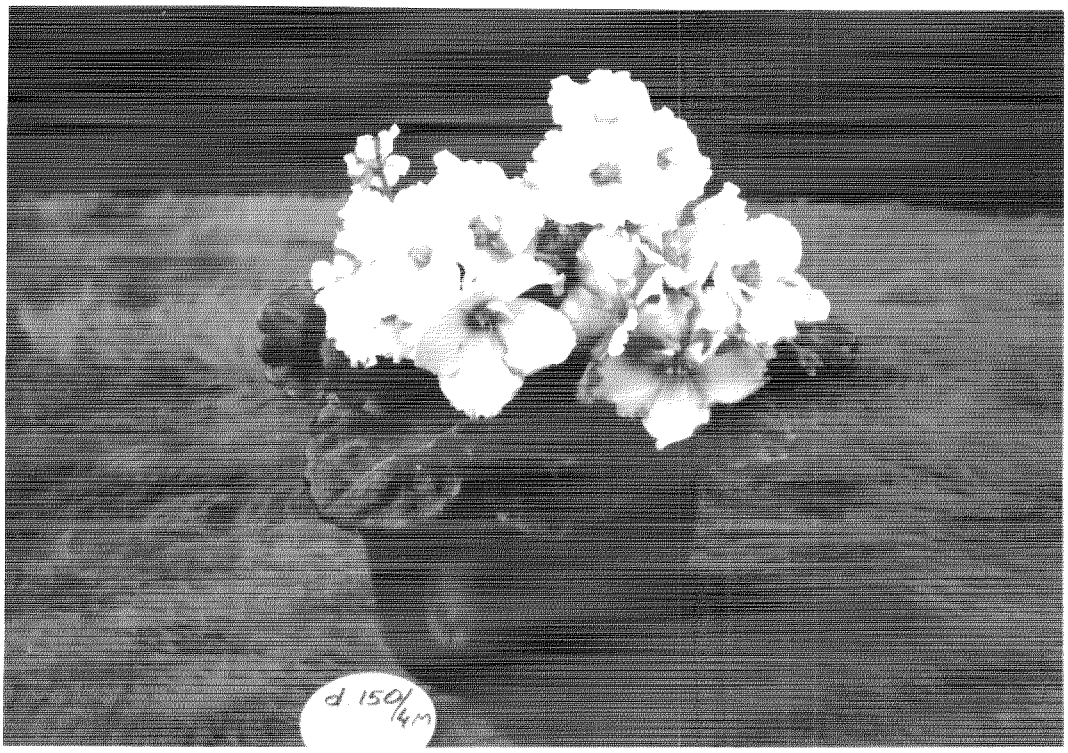
d. 150/4M